United States Patent
McClung, III

(10) Patent No.: US 9,479,741 B2
(45) Date of Patent: Oct. 25, 2016

(54) SYSTEM AND METHODS FOR DETECTING EFFORTS TO THWART MATERIAL DETECTION BY SERVICE ANIMALS

(71) Applicant: Guy Lamonte McClung, III, San Antonio, TX (US)

(72) Inventor: Guy Lamonte McClung, III, San Antonio, TX (US)

( * ) Notice: Subject to any disclaimer, the term of this patent is extended or adjusted under 35 U.S.C. 154(b) by 272 days.

(21) Appl. No.: 13/986,107

(22) Filed: Apr. 1, 2013

(65) Prior Publication Data

US 2014/0294728 A1    Oct. 2, 2014

Related U.S. Application Data

(60) Provisional application No. 61/686,384, filed on Apr. 4, 2012.

(51) Int. Cl.
| | |
|---|---|
| *A61K 33/00* | (2006.01) |
| *A61K 49/00* | (2006.01) |
| *H04N 7/18* | (2006.01) |
| *G06Q 99/00* | (2006.01) |

(52) U.S. Cl.
CPC ........... *H04N 7/188* (2013.01); *A61K 49/0004* (2013.01); *G06Q 99/00* (2013.01)

(58) Field of Classification Search
CPC .................... A61K 49/0004; H04N 7/188
USPC .............. 424/9.2, 76.1, 76.2, 76.21; 348/143
See application file for complete search history.

(56) References Cited

U.S. PATENT DOCUMENTS

| | | | |
|---|---|---|---|
| 2,203,188 A | 6/1940 | Beer | |
| 3,421,836 A | 1/1969 | Sundin et al. | |
| 3,750,556 A | 8/1973 | Duke | |
| 3,937,967 A | 2/1976 | Steinitz | |
| 4,045,316 A | 8/1977 | Legan | |
| 4,066,795 A * | 1/1978 | Dave | A23B 7/04 426/259 |
| 4,238,857 A | 12/1980 | Waters | |
| 4,309,388 A | 1/1982 | Tenney et al. | |
| 4,374,571 A | 2/1983 | Hirvela | |
| 4,500,510 A * | 2/1985 | Goldstein | A61K 31/715 424/744 |
| 4,569,749 A * | 2/1986 | Wright | C10G 1/002 208/413 |
| 4,863,687 A | 9/1989 | Stevens et al. | |
| 4,867,052 A | 9/1989 | Cipelletti | |
| 4,904,289 A | 2/1990 | Miyakami et al. | |
| 4,941,270 A | 7/1990 | Hoffman | |
| 4,953,674 A | 9/1990 | Landes | |
| 4,990,311 A | 2/1991 | Hirai et al. | |
| 5,087,426 A | 2/1992 | Inoue et al. | |
| 5,185,129 A | 2/1993 | Koutrakis et al. | |
| 5,192,500 A | 3/1993 | Treddenick | |
| 5,316,182 A | 5/1994 | Lee et al. | |
| 5,433,230 A | 7/1995 | Miller | |
| 5,433,919 A | 7/1995 | Baltes | |
| 5,468,454 A | 11/1995 | Kim | |
| 5,484,472 A | 1/1996 | Weinberg | |
| 5,514,345 A | 5/1996 | Garbutt et al. | |
| 5,539,930 A | 7/1996 | Sesselman | |
| 5,547,476 A | 8/1996 | Siklosi et al. | |
| 5,667,564 A | 9/1997 | Weinberg | |
| 5,681,355 A | 10/1997 | Davis et al. | |
| 5,762,648 A | 6/1998 | Yeazell | |
| 5,766,560 A | 6/1998 | Cole | |
| 5,789,368 A | 8/1998 | You et al. | |
| 5,790,987 A | 8/1998 | Sesselmann | |
| 5,833,740 A | 11/1998 | Brais | |
| 5,911,957 A | 6/1999 | Khatchatrian et al. | |
| 5,931,014 A | 8/1999 | Cole | |
| 5,972,714 A * | 10/1999 | Roland | G01N 33/0039 116/202 |
| 5,983,834 A | 11/1999 | Tai | |
| 6,007,770 A | 12/1999 | Peiper et al. | |
| 6,009,559 A | 1/2000 | Sesselmann | |
| 6,094,549 A | 7/2000 | Hiraoka et al. | |
| 6,134,718 A | 10/2000 | Sesselmann | |
| 6,149,038 A | 11/2000 | Tsai | |
| 6,156,268 A | 12/2000 | Curry et al. | |
| 6,163,098 A | 12/2000 | Taylor et al. | |
| 6,284,204 B1 | 9/2001 | Cole et al. | |
| 6,312,507 B1 | 11/2001 | Taylor et al. | |
| 6,336,964 B1 | 1/2002 | Omatsu et al. | |
| 6,340,497 B2 | 1/2002 | Wilson | |
| 6,355,216 B1 | 3/2002 | Kristiansson et al. | |
| 6,379,435 B1 | 4/2002 | Fukunaga et al. | |
| 6,503,547 B1 | 1/2003 | Lima | |
| 6,506,684 B1 * | 1/2003 | Daniel | H01L 21/02071 134/1.3 |
| 6,564,591 B2 | 5/2003 | Noyes | |
| 6,565,805 B2 | 5/2003 | Khatchatrian et al. | |
| 6,576,190 B1 | 6/2003 | Park | |
| 6,613,277 B1 | 9/2003 | Monagan | |

(Continued)

OTHER PUBLICATIONS

"Effects of Air Pollution on Olfactory Function in Residents of Mexico City," Chem. Senses 31, Hudson et al, Dec. 14, 2005, pp. 79-85.

(Continued)

*Primary Examiner* — Alma Pipic

(74) *Attorney, Agent, or Firm* — Guy McClung

(57) ABSTRACT

Methods and systems for detecting efforts to thwart the sense of smell of service animals and sniffer dogs. Methods and systems for detecting the introduction of and for neutralizing the effects of ONM introduced into an area. Methods and systems for the controlling the direction of the emission or ONM or descanter into an area. This abstract is provided to comply with the rules requiring an abstract which will allow a searcher or other reader to quickly ascertain the subject matter of the technical disclosure and is submitted with the understanding that it will not be used to interpret or limit the scope or meaning of the claims, 37 C.F.R. 1.72(b).

7 Claims, 7 Drawing Sheets

(56) References Cited

U.S. PATENT DOCUMENTS

| | | | |
|---|---|---|---|
| 6,632,407 B1 | 10/2003 | Lau et al. | |
| D486,357 S | 2/2004 | Leba et al. | |
| 7,117,687 B2 | 10/2006 | Naaman | |
| 7,118,608 B2 | 10/2006 | Lovell | |
| 7,222,634 B2 | 5/2007 | Hess et al. | |
| 7,514,008 B2* | 4/2009 | Burnes | C02F 1/008 210/746 |
| 7,662,636 B2 | 2/2010 | Maruo et al. | |
| 7,939,015 B1 | 5/2011 | Elrod | |
| 8,059,383 B2* | 11/2011 | Post | F04F 7/00 361/213 |
| 8,066,939 B2 | 11/2011 | Elrod | |
| 8,187,533 B2 | 5/2012 | Elrod | |
| 8,329,096 B2 | 12/2012 | Elrod | |
| 8,404,180 B1 | 3/2013 | Elrod | |
| 8,486,275 B2* | 7/2013 | Wolf | C02F 9/00 210/241 |
| 8,557,177 B1 | 10/2013 | Elrod | |
| 8,689,738 B2* | 4/2014 | Steffen | A01G 33/00 119/212 |
| 2002/0030022 A1 | 3/2002 | Bradley | |
| 2006/0096331 A1 | 5/2006 | Kim | |
| 2007/0092414 A1 | 4/2007 | Malyon | |
| 2010/0071633 A1* | 3/2010 | Elrod | 119/712 |
| 2012/0134876 A1 | 5/2012 | Elrod | |
| 2013/0125944 A1 | 5/2013 | Elrod | |
| 2013/0171022 A1 | 7/2013 | Elrod | |

OTHER PUBLICATIONS

"Photocopiers," www.workershealth.com, Nov. 15, 2007, 1 page.
"Neurotoxic Exposure and Olfactory Impairment," Clinics in Occupational and Environmental Medicine, Doty and Hastings, col. 1, No. 3, Aug. 2001; pp. 547-575.
"Ionizing Air Cleaners Can Cause Problems," Consumer Affairs, Apr. 12, 2055, 1 page.
"Ozone Generators What You Need to Know," Connecticut Department of Public Health, May 2007, 4 pp.
"Health Update: Ozone Generators Sold as Air Purifiers," ARC Board Meeting, Jan. 20, 2005, 11 pp.

* cited by examiner

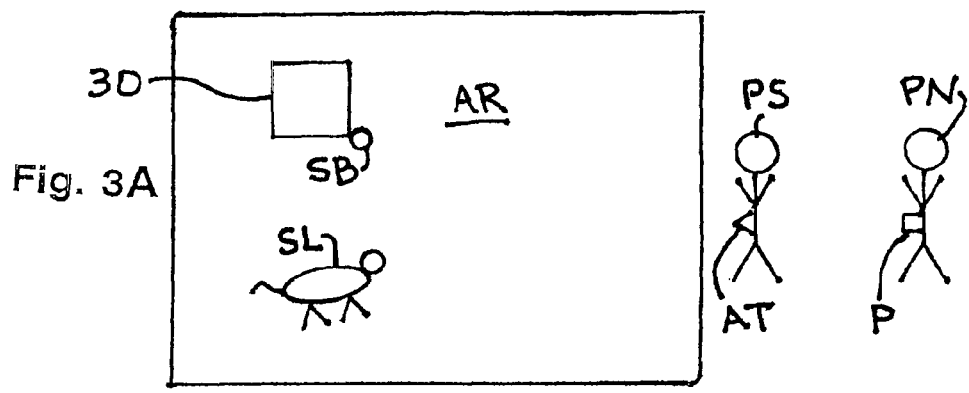
Fig. 3A
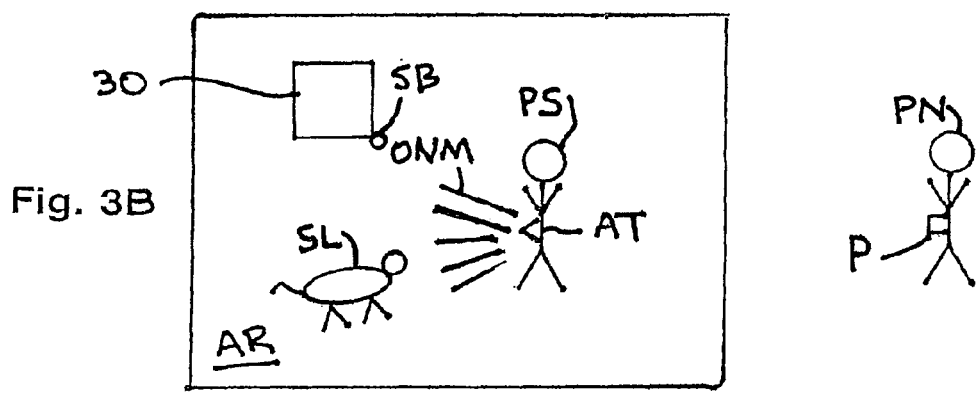
Fig. 3B
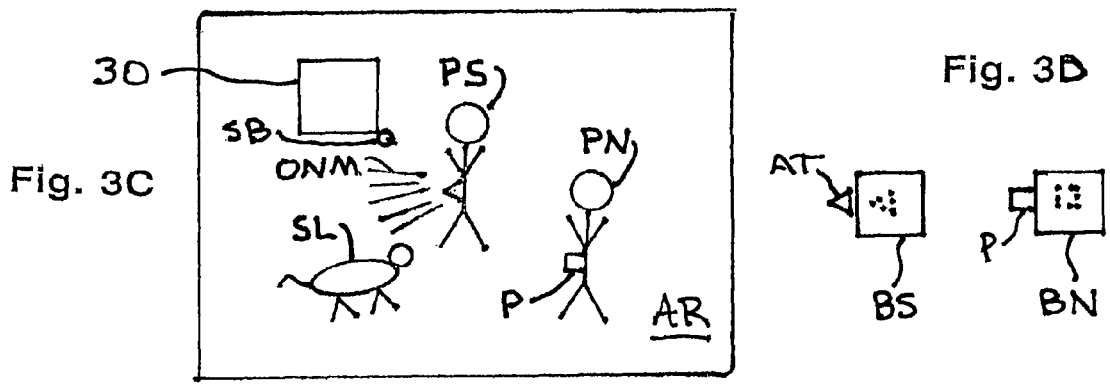
Fig. 3C
Fig. 3D

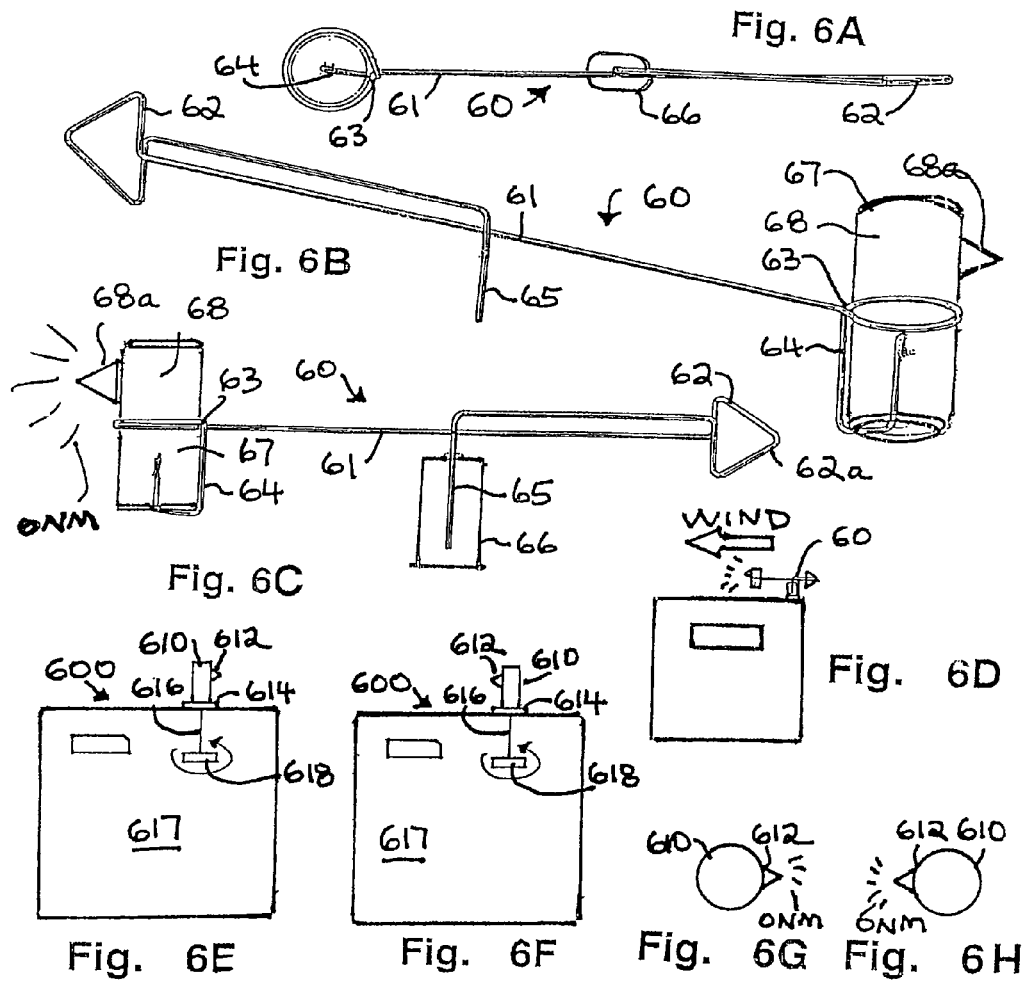
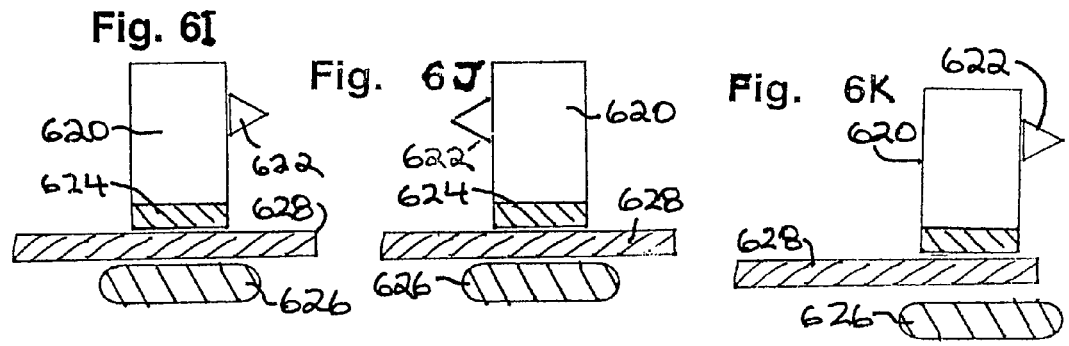

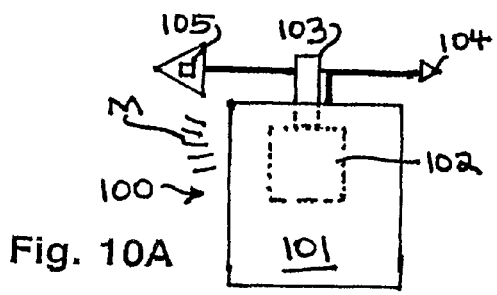
Fig. 10A
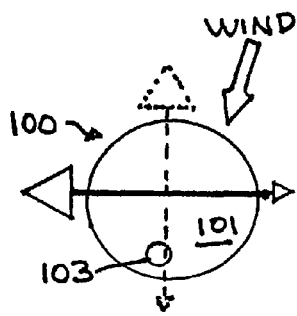
Fig. 10B
Fig. 11
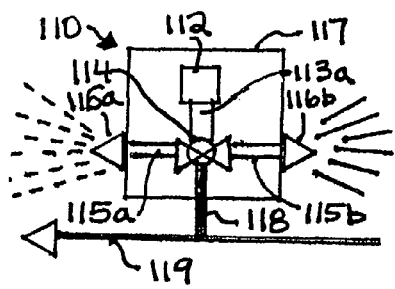
Fig. 12
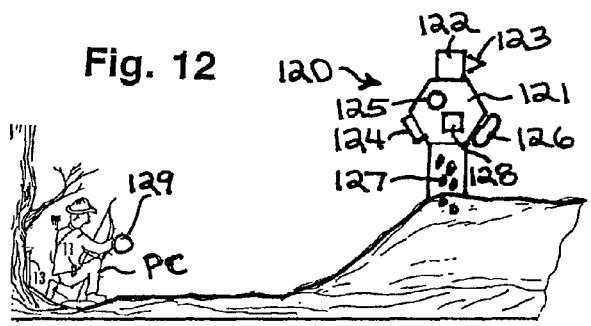
Fig. 13
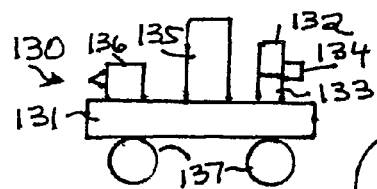
Fig. 14
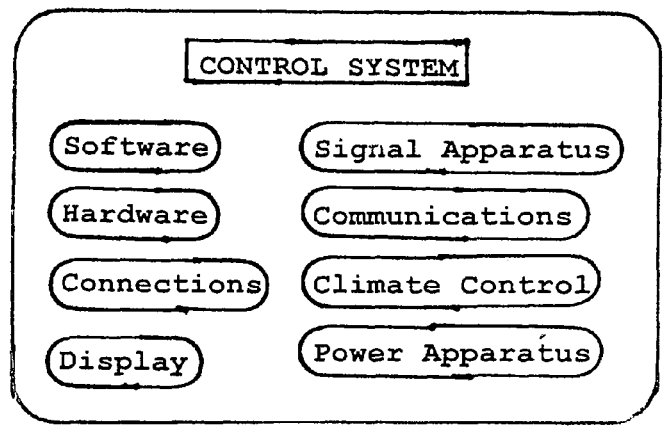

SYSTEM AND METHODS FOR DETECTING EFFORTS TO THWART MATERIAL DETECTION BY SERVICE ANIMALS

RELATED APPLICATION

This application claims the benefit of priority under the U.S. patent Laws of U.S. Application Ser. No. 61/686,384, Apr. 4, 2012, fully incorporated herein in its entirety.

BACKGROUND OF THE INVENTION

1. Field of the Invention

The present invention is directed to: systems and methods for detecting efforts to inhibit or nullify the olfactory function of a service animal or sniffer dog trained to detect material, substances, drugs, contraband, or explosives; methods for using such systems; systems and methods for neutralizing material used in an attempt to inhibit or nullify and animal's olfactory function; and systems and methods for locating a person and/or device attempting to thwart detection by such an animal or dog.

2. Description of Related Art

Service animals, search dogs and "sniffer" dogs are used in a variety of situations to detect and locate things such as dead bodies, cancer, drugs, substances, chemicals, contraband, explosives, and other materials. These methods rely on the acute and accurate sense of smell of these animals.

SUMMARY OF THE INVENTION

The present inventor has recognized that efforts could be made to inhibit, neutralize, nullify, or destroy (collectively referred to as "negate") the sense of smell, the olfactory function, of service animals used to detect materials, substances (chemical or biological), contraband, drugs, explosives, etc. These efforts may include the introduction into a service animal's environment of a substance, chemical, or material that will adversely affect the animal's olfactory function so that material, etc., cannot be detected by the animal.

It is within the scope of the present invention to provide systems and methods to detect and indicate when olfactory-nullifying material is used (collectively herein referred to as "ONM," e.g., substance or chemical) in whatever form it can be introduced (e.g., gaseous, vapor, liquid, solid, particulate) into an animal's environment and taken up by the animal—e.g., inspired, coated on the skin or organ surface, inhaled, taken through the nose, or taken by mouth—to negate the animal's olfactory function. ONM can include ozone, oxidizers, and chlorine and any other substance or chemical that can negate an animal's olfactory function.

In certain aspects, in methods according to the present invention, ONM is detected by suitable detector(s) and one or more of a variety of signals, alerts, notices, and/or alarms is provided to personnel and/or to service animals. In certain particular aspects, these alerts, etc., include visual notifications to personnel, audio alarms for an animal which humans cannot hear, and/or a visual cue to an animal. In other aspects, an oxidizer or oxidizing agent (e.g., but not limited to ozone) is detected, indicating an effort to negate the olfactory function of a service animal or the possibility of such an effort.

It is within the scope of the present invention to provide systems and methods to detect and indicate when olfactory-nullifying material is used (collectively herein referred to as "ONM," e.g., substance or chemical) in whatever form it can be introduced (e.g., gaseous, vapor, liquid, solid, particulate) into an animal's environment and taken up by the animal—e.g., inspired, coated on the skin or organ surface, inhaled, taken through the nose, or taken by mouth—to negate the animal's olfactory function. ONM can include ozone, oxidizers, and chlorine and any other substance or chemical that can negate an animal's olfactory function.

In certain aspects, systems according to the present invention provide a location of a source of ONM (and/or descanter and/or oxidizer) and/or a location of a person or persons who are introducing or dispersing ONM into an environment, or making an effort to negate the olfactory function of a service animal. In certain aspects, systems and methods according to the present invention are directed to situations in which, instead of a service animal, a machine, device, apparatus, system, or detector (collectively "machines") is used to monitor material presence and/or levels in an environment in which contraband, etc. might be located or might pass through. Such embodiments are like those described herein in which a service animal is included in the description, but, according to the present invention, a machine is substituted for the service animal and the systems and methods are directed at efforts to thwart the detection function of the machine. This is true for and includes every embodiment disclosed herein.

It is within the scope of the present invention for a person or persons (e.g., but not limited to, a hiker, hunter, sailor, photographer, videographer, naturalist, tracker, guide, soldier, sniper, birdwatcher) to use any system according to the present invention. It is within the scope of the present invention for such a person to use multiple systems according to the present invention, e.g., systems spaced-apart from each other and/or spaced-apart from the person.

Whenever a dog is referred to herein, it is within the scope of the present invention to use any service animal that can be used for detection, e.g., bird, cat, fish, pig, and dolphin.

Accordingly, the present invention includes features and advantages believed to enable it to advance detection technology for detecting efforts to thwart service animals and sniffer dogs or analogous machines.

Characteristics and advantages of the present invention described above and additional features and benefits will be readily apparent to those skilled in the art upon consideration of the following detailed description of preferred embodiments and referring to the accompanying drawings.

What follows are some of, but not all, the objects of this invention. In addition to the specific objects stated below for at least certain preferred embodiments of the invention, there are other objects and purposes which will be readily apparent to one of skill in this art who has the benefit of this invention's teachings and disclosures.

It is, therefore, an object of at least certain embodiments of the present invention to provide: New, useful unique, efficient, nonobvious systems for detecting efforts to thwart the use of detectors such as service animals, search dogs, and sniffer dogs used in detecting materials, substances (chemical or biological), drugs, contraband and explosives; and methods for employing such systems. In other aspects, this invention is directed to such systems and methods in which there is a machine instead of a service animal or sniffer dog.

It is, therefore, an object of at least certain embodiments of the present invention to provide such systems and methods which also provide a location of an apparatus and/or of a person who is attempting to inhibit, nullify, or destroy the olfactory function of a service animal (or the analogous function of a machine).

To one of skill in this art who has the benefits of this invention's teachings, other purposes will be appreciated from the descriptions herein when taken in conjunction with the drawings.

The detail in these descriptions is not intended to thwart this patent's object to claim this invention no matter how others may later disguise it by variations in form, changes, or additions of further improvements.

It will be understood that the various embodiments of the present invention may include one, some, or any possible combination of the disclosed, described, and/or enumerated features, aspects, and/or improvements and/or technical advantages and/or elements in claims to this invention.

BRIEF DESCRIPTION OF THE SEVERAL VIEWS OF THE DRAWINGS

A more particular description of embodiments of the invention briefly summarized above may be had by references to the embodiments which are shown in the drawings which form a part of this specification. These drawings illustrate embodiments preferred at the time of filing for this patent and are not to be used to improperly limit the scope of the invention which may have other equally effective or legally equivalent embodiments.

FIG. 3A is a schematic view of a system according to the present invention with two persons approaching the system.

FIG. 3B is a schematic view of the system of FIG. 3A with one of the persons in an area of a system according to the present invention.

FIG. 3C is a schematic view of the system of FIG. 3A with both persons in the area of the system according to the present invention.

FIG. 3D is a schematic view of things usable in and/or detectable by systems and methods according to the present invention.

FIG. 6A is a bottom view of a system according to the present invention for generating olfactory-nullifying material.

FIG. 6B is a perspective view of the system of FIG. 6A.

FIG. 6C is a side view of the system of FIG. 6A.

FIG. 6D is a side schematic view of a system according to the present invention.

FIG. 6E is a side schematic view of a system according to the present invention.

FIG. 6F is a side view of the system of FIG. 6E.

FIG. 6G is a top view of part of the system of FIG. 6E.

FIG. 6H is a top view of part of the system as shown in FIG. 6F.

FIG. 6I is a side schematic view of a system according to the present invention.

FIG. 6J is a side view of the system of FIG. 6I with part repositioned.

FIG. 6K is a side view of the system of FIG. 6I with part repositioned.

FIG. 10A is a side schematic view of a system according to the present invention.

FIG. 10B is a top view of the system of FIG. 10A.

FIG. 11 is a side schematic view of a system according to the present invention.

FIG. 12 is a side schematic view of a system according to the present invention.

FIG. 13 is a side schematic view of a system according to the present invention.

FIG. 14 is a schematic view of a control system according to the present invention.

Certain embodiments of the invention are shown in the above-identified figures and described in detail below. Various aspects and features of embodiments of the invention are described below. Any combination of aspects and/or features described below can be used except where such aspects and/or features are mutually exclusive.

It should be understood that the appended drawings and description herein are of certain embodiments and are not intended to limit the invention. On the contrary, the intention is to cover all modifications, equivalents and alternatives falling within the spirit and scope of the invention as defined by the appended claims.

Embodiments of the invention may be implemented, at least in part, either manually or automatically. Manual or automatic implementations may be executed, or at least assisted, through the use of machines, hardware, software, firmware, middleware, microcode, computers, hardware description languages, or any combination thereof.

When implemented in software, firmware, middleware or microcode, the program code or code segments to perform the necessary tasks may be stored in a machine readable medium. A processor(s) may perform the necessary tasks, e.g., but not limited to, computers, PLC's, laptops, desktops, smartphones, and tablet computers; including, but not limited to, any task or function of any control system, control system component, or detector described below.

DETAILED DESCRIPTION OF THE INVENTION

Figure 1:
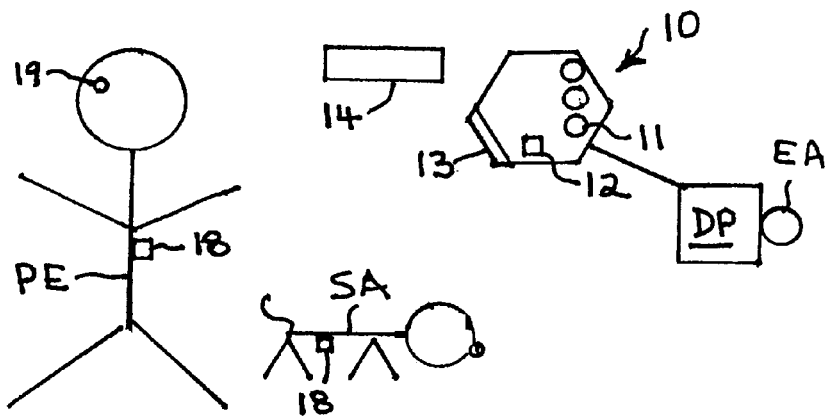
FIG. 1A is a schematic view of a system according to the present invention.
FIG. 1B is a schematic view of the system of FIG. 1A used in a method according to the present invention.
FIG. 1C is a schematic view of an optional apparatus for the system of FIG. 1A.
Figure 1:
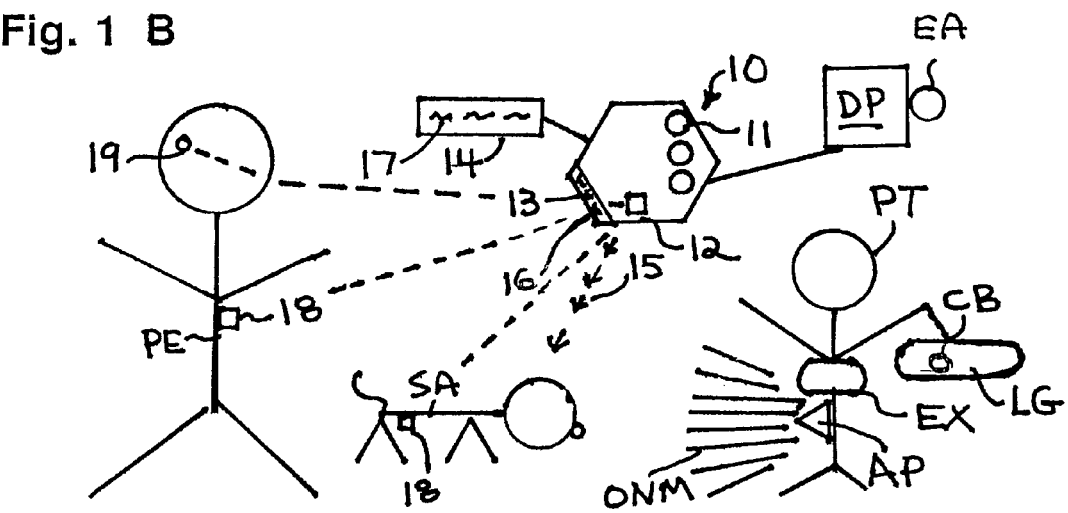
Figure 1:
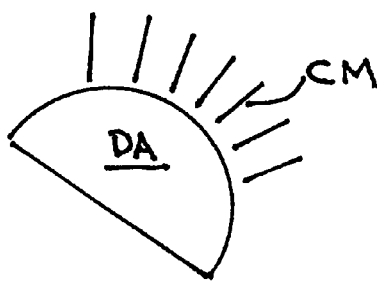

FIG. 1A shows a system 10 according to the present invention which has a sensor or sensors 11 for detecting olfactory-nullifying material (and/or descenter and/or reaction products); a signal apparatus 12 for providing signals, alerts, warnings, and alarms to a person PE and/or to a service animal SA; a screen or other visible device 13 for providing a visual alert to the service animal SA and/or to the person PE; and a screen or other visible device 14 for providing a visual alert to the service animal and/or to the person PE. Either or both screens may be deleted.

Optionally, the system 10 communicates with a communication device 19 used by the person PE which is, in one aspect, a cellphone, smartphone, computer or a private network communication device. The signal apparatus 12 of the system 10 can send signals, status updates, alerts, warnings, and alarms to the person PE via the device 19. Optionally, the person PE has a vibratory apparatus 18 which the system 10 controls and communicates with and which can be made to vibrate to convey a signal, an alert, a warning, an update, or an alarm to the person PE. Optionally, the device 19 may also provide this vibration function. Optionally, the service animal SA has a vibratory apparatus 18 which the system 10 controls and communicates with and which can be made to vibrate to convey a signal, an alert, a warning, or an alarm to the service animal SA.

As shown in FIG. 1B, a person PT desiring to thwart the service animal's efforts to detect material (drugs, chemical, radiological, or biological material), explosives EX and/or contraband CB in luggage LG, has activated an apparatus AP which emits ONM to adversely affect the olfactory function of the service animal SA. The audio apparatus 12 emits a sound (illustrated by the arrows 15) which, in one aspect, is only audible to the service animal SA and not to the persons PE and PT. The screen 13 displays a display 16 visible to the service animal SA and/or to the person PE. Optionally, the screen 14 provides a display 17 visible to the person PE and/or to the service animal SA.

In one aspect, the service animal SA is trained to respond to sound produced by the apparatus 12. The possible responses include responses evident to and of which the person PT and the person PE will be aware; a response of which the person PT will not be aware; and a response of which only the person PE will be aware.

In one particular aspect, the service animal is trained to sense the ONM and the service animal (which senses the ONM before it adversely affects the animal's olfactory function) provides an alert; e.g., but not limited to a sound (e.g., a bark), a movement, or a visual cue.

In one particular aspect, the apparatus AP is an ozone generator and the ONM is ozone in a sufficient amount to inhibit or nullify the olfactory function of the service animal SA. A detector 11 is capable of detecting ozone. In one aspect, the system 10 determines a threshold ozone level before arrival of the person PT and the system 10 continuously monitors the ozone level, noting an increase that indicates the introduction of additional ozone in the area of the person PT and, possibly, the operation of an apparatus such as the apparatus AP.

In one particular aspect, and as is true for any system and method according to the present invention, the level of ONM (e.g., but not limited to ozone or a reaction product of ozone with another material or substance) and/or its presence is noted and then the system monitors for an increase of the level of ONM to a level known to adversely affect the olfactory function of a service animal, e.g., but not limited to, a sniffer dog. Thus certain common causes of an increase of ONM or its addition to an area do not cause the issuance of a notice, alert or alarm and only an increase to an olfactory-nullifying level results in a notice, etc.

It is within the scope of the present invention to provide systems and methods that produce notices, alerts, signals, and/or alarms that are not detectable (visually or audibly) by persons involved in attempts to thwart detection by animals and/or those involved in crimes, sabotage, or terrorist acts. In other aspects, these notices, etc. are of such a nature and/or of such an extent and/or are at such a level that these persons are aware of the fact that their efforts have been detected.

Optionally, the signal apparatus 12 of the system 10 sends an audio signal and/or a vibratory signal to the apparatus communication device 19 used by the person PE which conveys information about the ONM, the fact that it is present, the location of the person PT, the possible location of the person PT, the location of the apparatus AP, and/or the possible location of the apparatus AP. In one aspect, the signal apparatus 12, in real time, sends signals to the person PE via the device 19 regarding ONM status updates and location (or possible location of the person PT and/or of the apparatus AP, alerts, warnings, and alarms. Optionally, the signal apparatus 12 activates the vibratory apparatus 18 of the person PE and/or of the service animal SA to convey a signal, an alert, a warning, an update, or an alarm.

so long as they are used in an operable fashion, and without contradicting another function, the system 10 and any part or parts thereof may be used in any other system according to the present invention and/or in any other method according to the present invention. Also, the service animal may be a dog or any other animal or creature that is used to sense material, contraband, or explosives; or instead of or in addition to an animal, a detector apparatus may be used to detect material, contraband, drugs, explosives etc. and, according to the present invention, efforts to thwart the operation of the detector apparatus are detected with systems and methods according to the present invention.

Optionally, the system 10 includes a detection apparatus DP which is dedicated to the detection of the presence of olfactory-nullifying material. This apparatus DP can activate the apparatus DA upon command from the system 10 or automatically upon the detection of ONM. Optionally, the apparatus DP is in communication with and/or includes evacuation apparatus EA for removing ONM.

In one aspect, the system 10 includes dispersal apparatus DA (see FIG. 1C) which disperses counteractive material CM that counteracts or neutralizes the ONM emitted by the person PT's apparatus AP. The type and amount of the material CM depends on the type and amount of the ONM.

Figure 2:
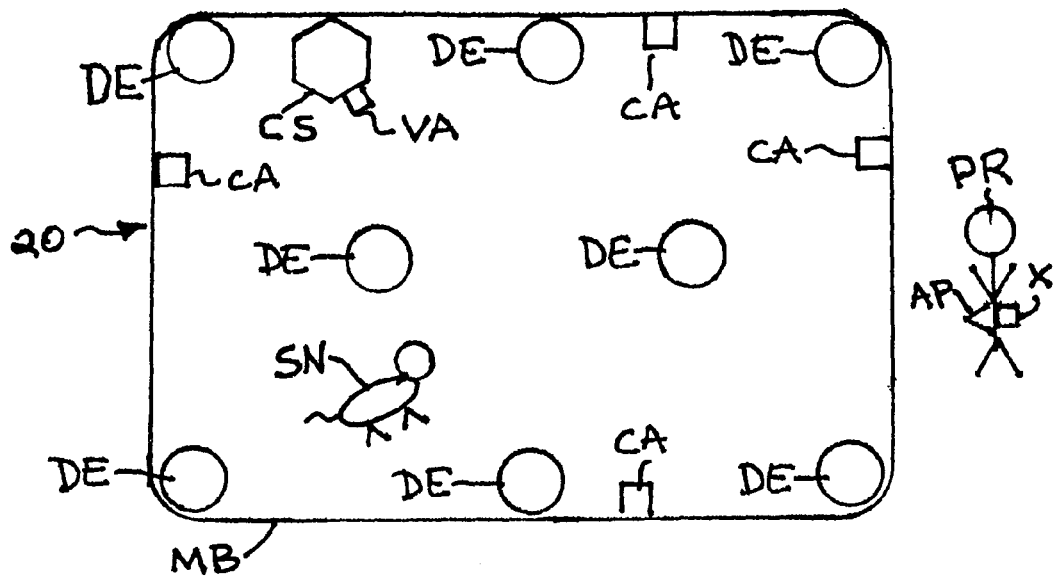
FIG. 2A is a schematic view of a system according to the present invention with a person approaching the system.
FIG. 2B is a schematic view of the system of FIG. 2A with the person among parts of the system.
Figure 2:
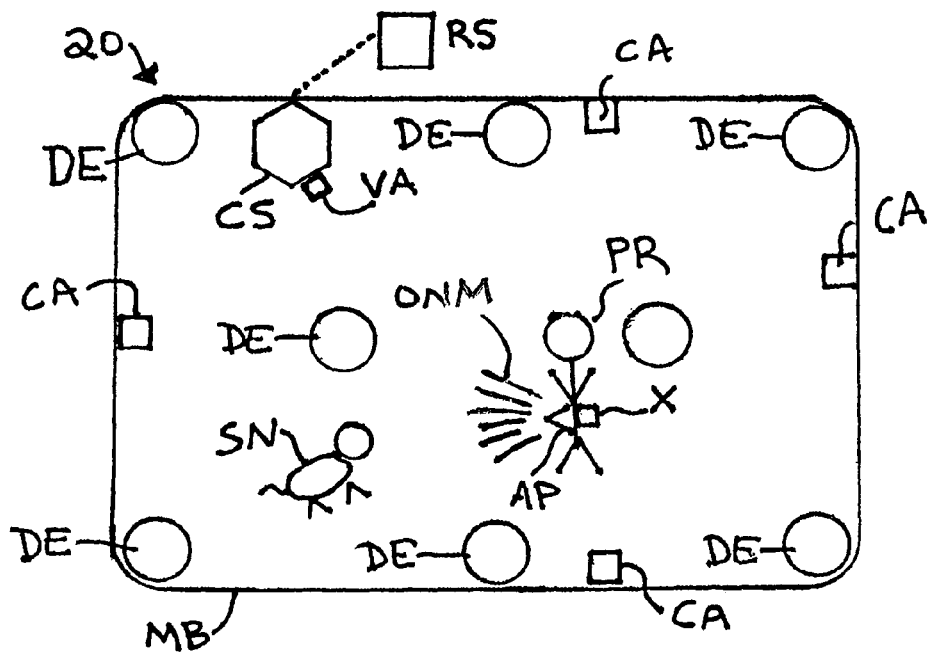

FIG. 2A shows a system 20 according to the present invention which is being approached by a person PR who has an apparatus AP (like that of FIG. 1A) and who is carrying a thing or substance X. The person PR will attempt to neutralize the olfactory function of a service animal SN that in normal circumstances is able to sense (using its olfactory system) the presence of the thing or substance X.

The system 20 includes a plurality of spaced-apart detectors DE which are capable of sensing ONM from the apparatus AP. A control system CS is in communication with the detectors DE and controls them. The service animal may have any of the devices and apparatuses of the service animal SA described above; and the control system CS may have any of the components of the system 10 and any of the devices and apparatuses associated with the system 10.

In one particular aspects, each detector DE senses initially a threshold level of ONM in the area of the system 20 (or the absence of ONM, i.e, a zero level) and then, over time (in one aspect, in real time) monitors the ONM level and sends signals to the control system CS indicative of ONM level. In other aspects, the detectors DE sense some other parameter which changes in response to ONM, rather than sensing the actual presence of ONM, and then they convey information about the level of this other parameter to the controls system CS.

Upon detection by the detectors DE of a change in ONM level (or detection of some other pertinent parameter or its change), the alerts, alarms, etc. described above for the system 10 may be initiated and transmitted.

In one aspect, the system 20, using information from the detectors DE, pinpoints the location of the person PR (or of the apparatus AP if the person has divested herself or himself of the apparatus AP). For example, as the person progresses across an area, the detectors DE sense the ONM as the ONM flows to them and over time the detectors DE sense different levels of ONM. Based on this information, the location of the person PR (or of the apparatus AP) is calculated and determined.

In one particular case, in which the apparatus AP is an ozone generator and the ONM is ozone, the detector DE closest to the person PR when the person PR enters the area of the system 20 is the first to detect the ozone and, as the person draws nearer to this first detector, the level of ozone detected by this detector increases. Meanwhile, other detectors are first detecting ozone and then detecting increased levels. The differentials between the time of initial detection and/or the detection of different levels provide the information for calculating the location of the source of the ozone and, hence, the location of the person PR and/or of the apparatus AP.

In one aspect (and as is true for any embodiment herein), the control system CS is in communication with a remote system RS (see FIG. 2B) which is remote from the area of the system 20. The remote system RS, in one aspect, controls the control system CS.

It is within the scope of the present invention for the detectors DE to be able to detect ONM emitted by the apparatus AP when the person PR is in a position such as that of FIG. 2A, and not yet between the detectors DE.

As is true for any embodiment hereof, the control system CS may include video apparatus VA for video monitoring of the area of the system 20. This video apparatus may include multiple cameras CA spaced-apart around the area of the system 20. Optionally, the area of the system 20 is an open area or, as shown in FIGS. 2A and 2B, a member MB may enclose the area (e.g., but not limited to a wall, partial wall, fence, barrier, structure, or panels), with suitable door(s) and/or entryways. Optionally, the system 20 includes dispersal apparatus, like the apparatus DA described above.

FIGS. 3A-3C illustrate a method according to the present invention in which a first person PS attempts to nullify the olfactory sense of a service animal SL in an area AR before a second person PN enters the area AR. The first person PS has an apparatus AT (like the apparatuses AP described herein) which disperses olfactory-nullifying material ONM to inhibit or destroy the olfactory function of the olfactory organs of the service animal SL so that the service animal SL does not detect a thing P (which may be a bomb, biological material, chemical material, contraband or explosives—as, for example, may be the contraband CB, FIG. 1B or the item X, FIG. 2A) carried by the person PN. A system 30 (which may be any system used in any embodiment of the present invention for detecting ONM and, optionally, for performing any additional function or functions disclosed herein) can detect the dispersion of ONM.

As shown in FIG. 3A, neither person has yet entered the area AR. As shown in FIG. 3B, only the person PS has entered the area AR. The person PS has activated the apparatus AT to begin dispersing ONM around the animal SL. The person PN waits until a pre-set time period has passed and/or until she or he receives a signal from the person PS (or from some remote controller and/or remote person) indicating that the olfactory function of the animal SL has been rendered inoperative.

As shown in FIG. 3C, the person PN has now entered the area AR carrying the thing P.

The system 30, as shown in FIG. 3A, has taken a threshold measurement of the level, if any, of ONM in the area AR (or noted its absence) before either person PS or PN has entered the area AR. Optionally, the system 30 measures the level (or absence or presence) of a material or substance SB that is a reaction product of ONM with the substance SB (as may be true for any system according to the present invention and any such system, instead of noting the presence of or measuring the level of ONM can note the presence of and/or measure the level of a reaction product of ONM with a known substance). The system 30 continues to monitor the level of ONM (or of the reaction product) over time.

When the person PS activates the apparatus AT and ONM is dispersed into the area AR, the system 30 notes the increase in the level of ONM (or its presence) which indicates either an effort to nullify the olfactory function of the animal SL or the possibility of such an effort. In response to this, the system (or the system 30 with any control system herein) can do a number of things, including, but not limited to:

continue to monitor the area;
determine the nature and amount of ONM;
calculate location of the person PS and/or apparatus AT, and/or of the person PN and/or of the thing P;
provide a signal to the animal SL which is non-olfactory so that the animal SL can then provide an alert or alarm;
activate camera(s), if not already operational, for monitoring and recording the area, the person PS, exits and entries to the area, and/or the animal SL and/or for taking photographs of the person PS, the apparatus AT, the person PN, and/or the thing P;
activate apparatus to introduce counteractive material for counteracting or neutralizing the ONM and/or for removing it from the area;
activate apparatus and/or devices to lock down the area and make entry and/or exit for any other person and/or any other thing impossible, in one aspect, to prevent entry of a person (like the person PN);
provide signal(s), alert(s), notice(s), and/or alarm(s) to personnel on site and/or remote from the area regarding the a person, like the person PS, the person PN, the dispersal of ONM, the nature of the ONM, and, if sensed, the nature of the thing P.

These functions envisage the possibility of a person, e.g., the person PS, divesting himself or herself of the apparatus AT in the area and/or the possibility of the person PN divesting himself or herself of the thing P in the area.

As shown in FIG. 3D, instead of a person (e.g., any of the persons in any drawing figure herein) an apparatus for dispersing ONM may be introduced into or put into an area by a thing; and a thing which is the subject of an attempt to avoid detection can be introduced into or put into an area by another thing rather than by a person. As shown in FIG. 3D, a thing BS has an apparatus AT (like that of FIG. 3A) on it (or in it as shown in dotted line) and the thing BS is moved, dropped, secreted or transported into the area of a system according to the present invention, e.g., like the area AR. As shown in FIG. 3D, a thing BN has an thing P (like that of FIG. 3A) on it (or in it as shown in dotted line) and the thing BN is moved, dropped, secreted or transported into the area of a system according to the present invention, e.g., like the area AR. The thing which carries or contains contraband, etc., may be, but is not limited to, luggage, package, container, vehicle, hollow member, box, bag, or envelope.

It is within the scope of the present invention to provide systems and methods which detect efforts to nullify the olfactory function of service animals in efforts to transport and/or use material (chemical, radiological or biological), explosives, drugs, and/or contraband and then allows a carrier of the material etc. to proceed beyond, spaced-apart from, remote from, or past a point of detection to another location (apart from the point of initial detection) for interdiction, stoppage, arrest, or disposal.

Figure 4:
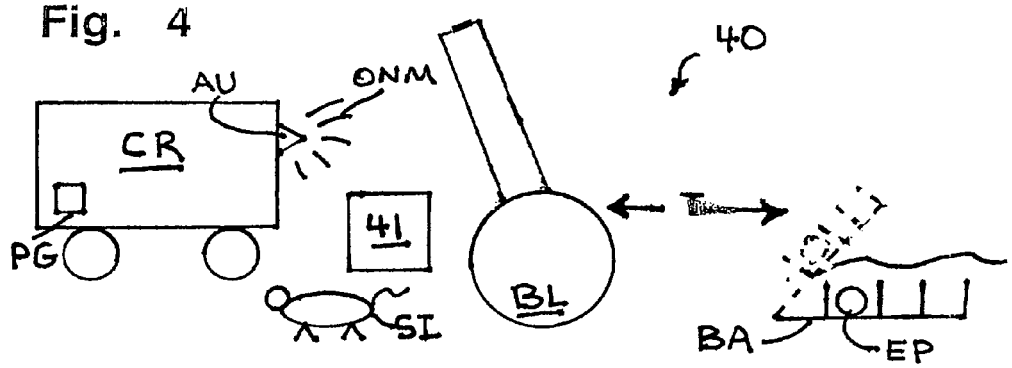
FIG. 4 is a schematic view of a system and method according to the present invention.

As shown in FIG. 4, a system 40 according to the present invention has a blocking structure BL or apparatus for blocking a carrier CR and a system 41 for detecting the presence and/or level of ONM. A sniffer dog SI is at the location of the system 40 for detecting certain material PG (e.g., but not limited to, drugs or explosives). If the carrier CR has apparatus AU that emits ONM, the system 41 senses this (although the dog SI may not detect the material PG due to the adverse effect of the ONM on the dog's olfactory organs).

In order to protect property and personnel at the location of the structure BL, the carrier CR is allowed to pass and proceed a distance T from the structure BL. At this point a stopping apparatus, blocker, or barrier BA is activated which stops the carrier CR. In one aspect, as shown in FIG. 4, the barrier BA is initially underground, but is moved above ground (see dotted lines) to stop the carrier CR. Optionally, explosives EP are detonated adjacent the carrier CR to destroy it and/or the material PG.

The carrier CR may be any known vehicle, automobile, tank, personnel carrier, drone, glider, transporter, boat, plane, helicopter, trailer, snowmobile, robot, tracked vehicle, wheeled transport, raft, train, subway, hovercraft, or truck. In one particular aspect, the carrier CR is a person or an animal. In one particular aspect, the system 40 is used when no service animal or sniffer dog is present. In one particular aspect, the blocking structure BL is at a train station, airport, subway station, terminal (train, subway, or airport), or bus station.

It is within the scope of the present invention to provide systems and methods for facilitating the hunting of animals and the viewing of animals in the wild. An ONM generator is provided at a location at which it is anticipated animals may be, or at a location at which it is anticipated animals will move through. The generator produced sufficient ONM that the olfactory organs of the animals do not provide the usual warning of the presence of other animals, e.g., humans (e.g., a photographer, videographer, or hunter.) Although the humans can employ efforts to descent themselves, their gear, and their clothing, this is unnecessary if the animals are unable to smell the humans, their gear, and their clothing.

Figure 5A:
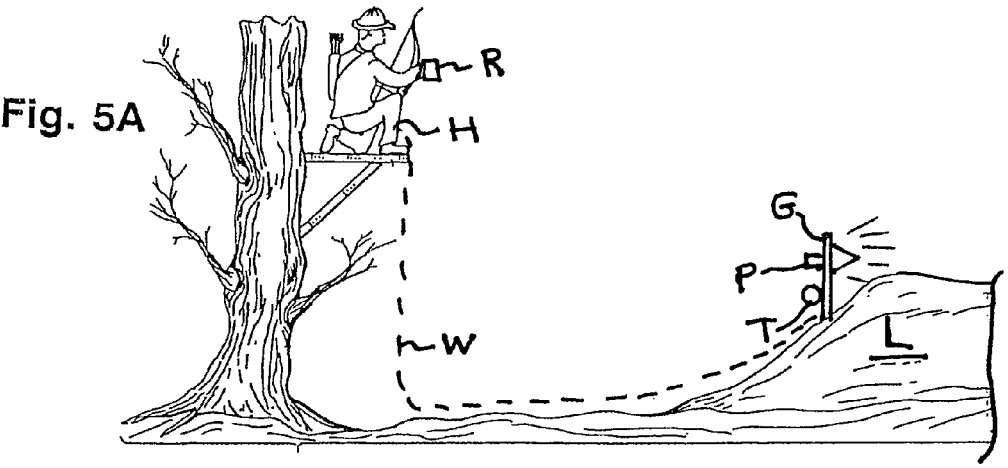
FIG. 5A is a schematic view of a system according to the present invention.

FIG. 5A shows a system 50 according to the present invention which has an ONM generator G that a hunter H has placed at a location L to which he expects an animal to come. Optionally, the generator G has a timer that turns it on and off at pre-selected times. Optionally, the generator G has a solar power supply P. Optionally, the hunter H has a remote control R that allows him to control the generator G remotely, e.g, from a blind or, as shown, from a tree. Optionally, a wire or cable W (shown in dotted line, FIG. 5A) provides control of the generator G.

Figure 5B:
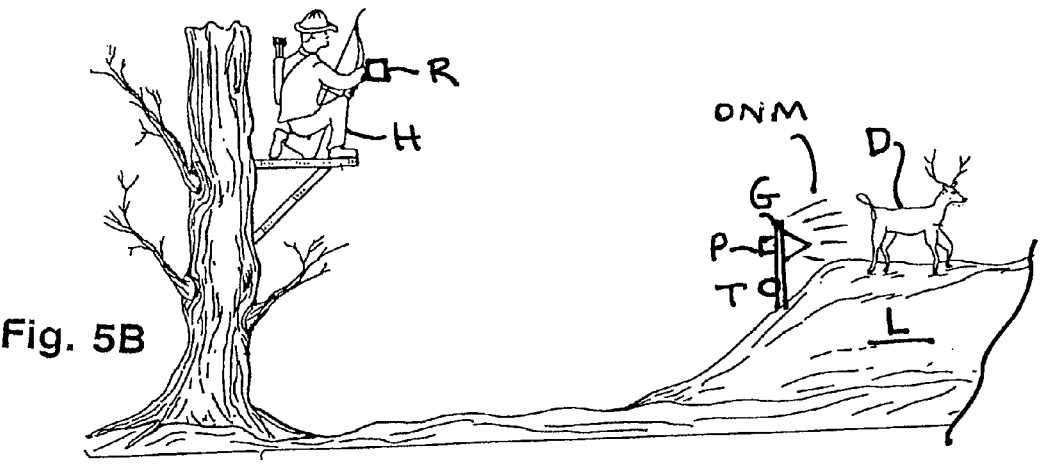
FIG. 5B is a schematic view showing use of the system of FIG. 5A.

In one aspect, the hunter H takes his position in the tree and, using the remote control R, activates the generator G. As shown in FIG. 5B, the generator G emits ONM. In one aspect, the olfactory function of a deer D at the location L is impacted to the extent that the deer D does not smell the hunter H or his gear or clothing—and this is true whether or not the hunter has made any effort to hide himself or to descent himself or his things; and the hunter's relative location to the animal, upwind, downwind, or otherwise, does not matter. In one aspect the person H is not a hunter, but is a photographer or videographer intent on filming animals.

In one particular aspect, the ONM is ozone present at a sufficiently high level to negate, inhibit or temporarily nullify the olfactory function of the animal. In one particular aspect, the ONM is chlorine present at a sufficiently high level to negate, inhibit or temporarily nullify the olfactory function of the animal. In one particular aspect, the ONM is an oxidizer present at a sufficiently high level to negate, inhibit or temporarily nullify the olfactory function of the animal. All of these materials may be the subject of any embodiment of the present invention.

It is within the scope of the present invention to provide an apparatus that includes an ONM generator and a weather vane structure to maintain an output of the ONM generator so that the ONM is directed in a generally downwind direction. By suitable placement of the ONM generator and its material output structure at a large end or on a large part of a weathervane structure, when the weathervane structure moves in response to wind, the ONM generator's output structure will be pointed in the direction of the wind. This will occur relatively soon after there is sufficient wind to move the weathervane structure or relatively quickly after a change in wind direction. This will also relieve a person (e.g., hunter, photographer, videographer) from having to pay attention to wind direction and from having to periodically reorient an ONM generator when the wind direction changes.

FIGS. 6A-6C show a weathervane system 60 according to the present invention that has a main member 61, a front member 62 with an end 62a, a rear member 63, and a holding structure 64. A shaft 65 is connected to or formed of the main member about which the weathervane 60 can rotate in response to the wind; and, optionally, the shaft is rotatably mounted in a base which can be placed in any desirable location or any desirable structure. An ONM generator 67 is releasably held by the holding structure 64.

In one particular aspect, the ONM generator 67 is an ozone generator (which may be or may be like any such generator disclosed herein or in references cited herein) which is capable of emitting sufficient ONM to inhibit, neutralize, or nullify the olfactory function of an animal sought to be viewed or hunted. The generator 68 has an output structure 68a from which ONM is emitted, pointing generally in the direction indicated by the lines labeled ONM in FIG. 6C. When wind impacts the weathervane system 60, the weathervane will rotate so that the end 62a points in the direction from which the wind is coming and the structure 68a emits ONM in a downwind direction; i.e., due to the action and positioning of the weathervane in response to the wind ONM is dispersed in a direction downwind from the generator 68 and downwind from a location of the system 60.

FIG. 6D illustrates the emplacement of a system 60 on a blind 69 which, in response to the wind (indicated by the arrow labeled "WIND") has rotated so that ONM is dispersed downwind from the blind (and downwind from any person or thing within the blind).

In other aspects, the generator 68 generates descenter, whether it is ONM or not, whether or not it is in sufficient amounts to inhibit, neutralize, or nullify and animal's olfactory function; e.g., in one aspect, such a generator simply emits descenter to descent a person and/or a thing. This is also true and also possible for the embodiment of FIGS. 6E-6H—i.e., that the generator emit descenter whether or not it emits ONM.

It is within the scope of the present invention to provide an ONM generator system (and/or a descanter emitting system) which can be placed on one side of a structure (e.g., but not limited to, blind, roof, wall, tent, house, shed, lean-to, treehouse) with a movable member that extends to the other side of the structure so that an output of the ONM generator can be moved as desired from within the structure without the need for a person to exit the structure to reposition the generator.

In one embodiment, a system 600 as shown in FIGS. 6E and 6F has a structure 617 with an ONM system 610 placed on a top of the structure. A shaft 616 connected to the system 610 extends through the structure into its interior wherein a person can manipulate a handle 618 connected to the shaft 616 to change the position of the system 610. Thus the general direction to which ONM emitted through an output 612 of the system 610 can be changed from within the structure 617.

As shown in FIG. 6F, the handle 618 has been turned and the system 610 has been rotated so that the output 612 points in a direction opposite to that to which it pointed in as shown in FIG. 6E. This difference is shown in FIGS. 6G and 6H, FIG. 6G corresponding to the direction of the system in FIG. 6E and FIG. 6H corresponding to the direction of the system in FIG. 6F.

It is within the scope of the present invention to provide a system, either for dispersing ONM or for dispersing descenter, which can be moved and rotated from within a structure using magnetic attraction and magnetic force. Either the system has a magnetically attractive part which is outside the structure and a magnet or magnetic force apparatus inside the structure placed adjacent the system's magnetically attractive part; or the system has a magnet or magnetic force apparatus (e.g., but not limited to, an electromagnet apparatus) which is outside the structure and a magnetically attractive member is inside the structure placed adjacent the system's magnet or magnet force apparatus.

In the one aspect, movement of the magnet (or magnet apparatus) inside the structure moves the system on the outside of the structure; and in the other case, movement of the magnetically attractive part inside the structure results in the movement of the system on the outside of the structure. The movement can be used to rotate a system and/or to reposition it.

As shown in FIGS. 6I and 6J, a system 620 for emitting ONM or for emitting descenting material is on the outside of a structural member 628 and a magnet 626 in on the inside. The system 620 has a magnetically attractive part 624 which can be attracted to the magnet 626 and the magnet 626 is of sufficient magnetic strength to move the system 620.

As shown in FIG. 6J, the magnet 626 has rotated the system 620 so that an output 622 through which ONM or descenter flows is pointed in a direction different from that to which it pointed as shown in FIG. 6I. Optionally, the magnet 626 is left in place to hold the system 620 in place on the outside of the structural member 628.

It is within the scope of the present invention for the roles of the two parts to be reversed; i.e., for the part 626 to be made of magnetically attractive material and for the part 624 to be the magnet or the magnetic force apparatus.

FIG. 6K illustrates movement of the system 620 by the magnet 626 without rotation of the system 620.

Figure 7:
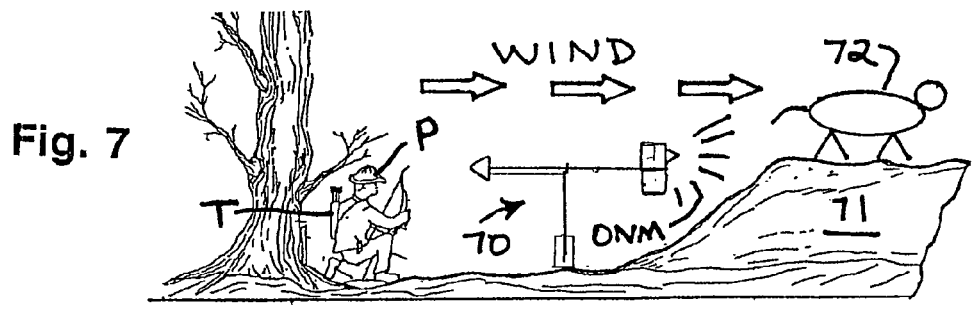
FIG. 7 is a schematic view of use of a system according to the present invention, e.g., like the system of FIG. 6A.

As shown in FIG. 7, a system 70 according to the present invention (e.g., like the system 60 described above) is placed at or near an area 71 at which it is anticipated an animal 72 may appear or pass through. With or without wind, the system 70 emits ONM (or descenter, or both). When wind commences, in the direction indicated by arrows labeled "WIND," the system 70 moves in weather-vane fashion so that an output of ONM (or of descenter) from the system 70 is directed at the area 71. As is true for each system herein, in one aspect, the system 70 emits sufficient ONM to negate the olfactory function of the animal 72.

In the case in which the system 70 emits descenter, scent from a person P and/or from things T on or near the person P will pass through descenter material emitted by the system 70 and the scent or scents will be descented, inhibiting detection of the person P by the animal 72.

Figure 8A:
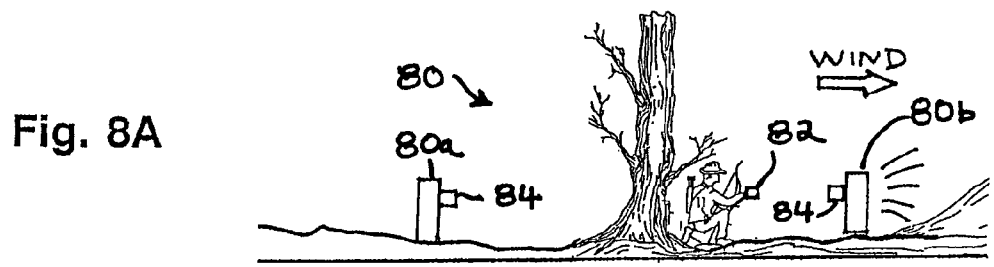
FIG. 8A is a side schematic view of a system according to the present invention for generating olfactory-nullifying material.
Figure 8B:
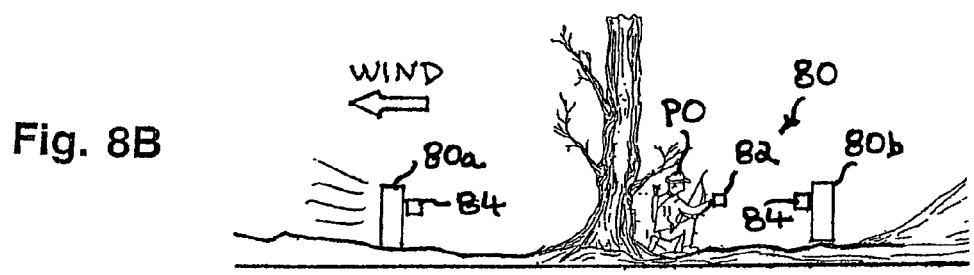
FIG. 8B is a side schematic view of the system of FIG. 8A.

It is within the scope of the present invention for a person (e.g., but not limited to, a hiker, hunter, sailor, photographer, videographer, naturalist, tracker, guide, soldier, birdwatcher) to use any system according to the present invention. It is within the scope of the present invention for such a person to use multiple systems according to the present invention, e.g., emitting systems spaced-apart from each other and/or spaced-apart from the person. As shown in FIGS. 8A and 8B, a person PO is located between two systems 80a and 80b according to the present invention (which may each be any system disclosed herein according to the present invention for emitting ONM and/or descanter).

In one aspect, a person such as the person PO is situated so that when wind blows in one direction, one of the multiple systems emits material in the direction of the wind and not in the direction of the person. When the wind changes, a different system according to the present invention emits material in the new direction of the wind, and not in the direction of the person.

For example, as shown in FIGS. 8A and 8B, in FIG. 8A the wind is blowing in an initial direction (right to left as shown in FIG. 8A); and the system 80b is emitting material in the direction of the wind, a direction away from the person PO. When the wind direction changes, as shown in FIG. 8B, the system 80a emits material in the direction of the wind, and not in the direction of the person PO and, optionally, the system 80b is shut down so that it no longer emits material. Optionally, the system 80b may remain on. Thus it is insured that material is emitted downwind of the person PO when wind direction changes; and, in one aspect when one system is shut down, that no system feeds material onto and/or past a person to a desired area.

It is within the scope of the present invention for any system according to the present invention to be remotely controlled, either by a person near, but not in, an area into which material is to be emitted; or by a person far away from the desired area, e.g., but not limited to, with video monitoring of the desired area.

Optionally, as shown in FIG. 8A, the person PO has a remote control device 82 and the systems 80a and 80b have corresponding remote control apparatus 84 with which the device can communicate. These can be wired or wireless remote control systems. For whatever reason, including, but not limited to a change in wind direction, the person PO can turn one or both of the systems 80a and 80b on or off.

Figure 9A:
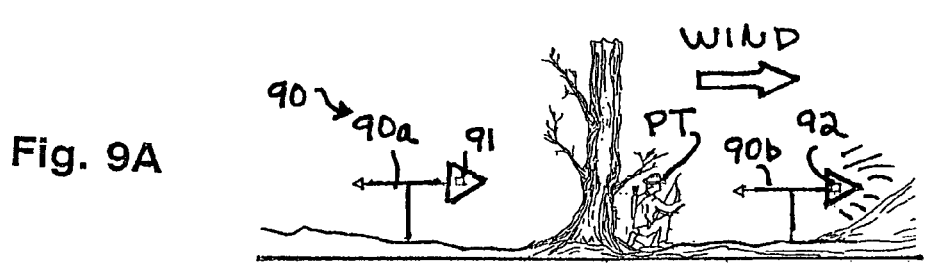
FIG. 9A is a side schematic view of a system according to the present invention for generating olfactory-nullifying material.
Figure 9B:
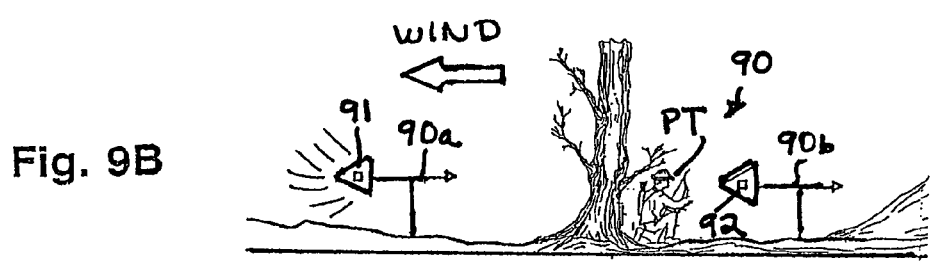
FIG. 9B is a side schematic view of the system of FIG. 9A.

FIGS. 9A and 9B illustrate the use of multiple systems 90a and 90b according to the present invention by a person PT. These systems utilize the weathervane structure and functions of weathervane systems according to the present invention and may be like any weathervane system disclosed herein according to the present invention. The system 90a has a material-emitting system 91 (like any material-emitting system herein) and the system 90b has a material-emitting system 92 (like any material-emitting system herein).

In one aspect, with wind blowing in the direction indicated in FIG. 9A, the system 92 of the system 90b emits material (ONM and/or descanter) in the direction of the wind. Optionally, the system 90a is not operating at this time; or, in another aspect, the system 90a is operating. With wind blowing in another direction indicated in FIG. 9B, the system 91 of the system 90a emits material (ONM and/or descenter) in the direction of the wind. Optionally, the system 90b is not operating at this time; or, in another aspect, the system 90b is operating. As is true for any system according to the present invention, it is within the scope of the present invention for the person PT (and/or some other persons or persons) to remotely control the systems 90a and 90b.

It is within the scope of the present invention for a system according to the present invention for emitting material (ONM and/or descenter) to include apparatus and/or structure for ceasing material emission in response to a change in wind direction without personal monitoring of the wind and without action by a person using the system. Any known apparatus, device, structure, circuit, switch, and/or switching system may be used to effect deactivation of the system including, but not limited to, contact of a weathervane part to complete or interrupt a circuit, or such contact of a part connected to a weathervane; completion (or interruption) of an electrical circuit using part of a weathervane; and/or contact of a weathervane part or part connected thereto with a movable switch or pushbutton device for moving or activating/deactivating the switch or for completing or interrupting a circuit.

FIGS. 10A and 10B show a system 100 according to the present invention which has a base 101 and a material-emitting system 102 (like any such system herein according to the present invention for emitting ONM, descanter, or both). A switch device 103 is operable to turn the system 102 on and off, to commence or stop the emission of material. A weathervane apparatus 104 is rotatably mounted to the base 101 and rotates in response to wind.

As shown in FIGS. 10A and 10B, the weathervane apparatus 104 is not initially in contact with the switch device 103 and the system 102 is emitting material M as shown in FIG. 10A. As shown in dotted line in FIG. 10B, in response to a change in wind direction, the weathervane apparatus 10 has rotated to the extent that part of it has contacted the switch device 103 and, as a result of this contact, the switch is moved or activated resulting in the cessation of the emission of material from the system 102. Optionally, the weathervane apparatus 104 has a material-emitting system 105 according to the present invention (any disclosed herein) in addition to or instead of the system 102.

It is within the scope of the present invention for a material-emitting apparatus according to the present invention to have multiple emission structures so that emitted material is directed in the direction of one of several directions depending on the particular emission structure chosen. Selective apparatus is provided which allows a person or a control apparatus to choose one of several directions to which material is emitted. Any suitable known channel selection apparatus or valving system may be used to achieve this direction selectability.

FIG. 11 illustrates a system 110 according to the present invention which has a housing 117 with a material-emitting system 112 according to the present invention (any system disclosed herein according to the present invention). Emitted material flows in a first channel 113a to a valve apparatus 114 which is operable by a part 118 or a weathervane apparatus 119 to permit material flow to either a channel 115a or a channel 115b—these channels in fluid communication with output structures 116a and 116b, respectively, which direct material in opposite directions.

In one aspect, the valve apparatus 114 has one position in which it permits material flow to both channels 115a and 115b. In another aspect, instead of the part 118, electronic devices sense wind direction and/or weathervane position and control the valve apparatus 114.

It is within the scope of the present invention to provide a system for acclimating an animal to an area and/or for attracting an animal to an area which is then is treated with ONM and/or descanter or which prior to arrival of an animal is treated. The attractant may be a chemical attractant, smell attractant, visual attractant, food attractant, or sound attractant. Such a system may be remotely controlled. Such a system can be activated by a timer for periodic activation or for activation prior to an expected arrival time of a person at the area and/or of an animal to be viewed or hunted at the area. Such a system, and any part of it (attractant dispenser or provider; ONM or descanter emitting; timer) can be activated by a sensor that senses the presence of an animal.

FIG. 12 illustrates a system 120 according to the present invention which has an attractor system 121 which emits animal attractant 127. The system 120 may operate continuously or, optionally, the system 120 includes a timer system 125 which activates the system 120 at a preset time or times to emit attractant (e.g., daily, multiple times in one day, every other day, every third day, every fourth day, weekly, monthly). A person PC can control the system 120 remotely with a remote control device 129 which communicates with a remote control apparatus 124 on the system 120.

Optionally, the system 120 is activated by a sensor system 126 which senses the presence of an animal' or, optionally, the system 120 is activated only in the case in which the sensor system 126 indicates no animal of interest is present. Optionally, the system 120 has a camera system for monitoring the system 120 and/or the area around the system 120. It is within the scope of the present invention for any system according to the present invention to have any of the systems, devices, apparatuses, or features of the system 120 or associated with the system 120.

It is within the scope of the present invention to provide in or on a vehicle any of the systems according to the present invention (including, but not limited to, any system that emits material and any system that detects material); the "vehicle" including, but not limited to, a drone, plane, helicopter, glider, automobile, tank, train, personnel carrier, transporter, boat, subway, raft, snowmobile, tracked vehicle, robot, trailer, wheeled transport, hovercraft, or truck. Such a vehicle may include: a power system, steering system, communication system, remote control system, ONM emitting system, descenter emitting system, and/or detector system. Any such a vehicle may also include any of the features, apparatuses, aspects, structures, or devices of any system shown in any drawing herein.

As shown in FIG. 13, a system 130 (which may include all or part of any system herein) has a detector 135 on a vehicle 131 (which may be any vehicle referred to in the preceding paragraph). The vehicle may include wheels and/or tires 137. The vehicle may include power apparatus 132 for powering the vehicle (e.g. any suitable power plant, motor, engine) and steering apparatus 133. Optionally, the vehicle is remote controlled using remote control apparatus 134. Optionally, the vehicle has material emission apparatus 136 which may emit ONM, descenter, and/or oxidizer (and which may be any emission system disclosed herein). The detector 135 may be any detector or detectors disclosed herein.

Any system according to the present invention that has a detector for detecting ONM may have any suitable known detector for detecting ONM; any system according to the present invention that has a detector for detecting descenter may have any suitable known detector for detecting descenter; and a any system according to the present invention that has a detector for detecting a reaction product may have any suitable known detector for detecting reaction product—including, but not limited to, any suitable system or apparatus for detection disclosed in or in references referred to in these U.S. patents and U.S. patent applications: U.S. Pat. Nos. 7,850,833; 7,813,820; 7,792,126; 7,655,887; 7,578,974; 7,565,255; 7,236,083; 7,193,187; RE 37,745; 5,797,358; 5,203,687; 4,805,122, 4,793,799; 4,601,293; 4,586,149; 4,409,590; 4,185,604; and U.S. Applications Publication Nos. 20100289655; 20100140478; 20100078560; 20100011836; 20090183552; 20090043515; 20070192041; 200602500261; 20060228266; 20050173635; 20050100478; and 20040231399; and any suitable known control system may be used with such detectors and/or detection systems, including, but not limited to, any disclosed herein and any disclosed in any of the patents and applications listed above or in the references in these patents and applications. In one aspect, such a control system—illustrated schematically in FIG. 14) has software; hardware (including, but not limited to, processors and memory); connections (wiring, cables, circuits); signal apparatus (calculators, processors, memory, receivers, transmitters); communications apparatus (for communicating with every component and each person, on-site or remote); climate control (heating, cooling); power apparatus (generation, connections, control, optionally solar power); and/or display (screens, speakers, chart apparatus, alarm system, printer). Such a system can have apparatus for automatic control, manual control, and/or remote control and can have apparatus to effect any function disclosed herein for any system according to the present invention.

It is within the scope of the present invention to provide a computer-readable medium for executing an instruction or instructions to effect any step or function, or all steps or functions, of each method herein and/or to effect any method according to the present invention. It is within the scope of the present invention to provide a computing unit to read and perform any such instruction(s).

All patents and applications referred to herein are incorporated fully herein for all purposes.

What is claimed is:

1. A method for detecting an effort to thwart effective operation of a detector, the detector comprising a detector of first material, the method comprising a person introducing a nullifying material in an area in which a detector of first material is located, wherein the nullifying material is for adversely impacting operation of the detector of first material so that detection of first material by the detector of first material is inhibited or prevented, and wherein the nullifying material is one of ozone, chlorine, or an oxidizer;

detecting introduction of the nullifying material; and controlling the detector with a control system, the control system providing functions of monitoring presence of the nullifying material in the area, determining an identity of the nullifying material in the area, determining a location within the area of the nullifying material being introduced into the area, determining a location within the area of the person who is introducing the nullifying material into the area, providing a signal to an animal which is a non-olfactory signal so that the animal can then provide an alert or alarm, activating a camera for monitoring and recording the area, and exits and entries to the area of persons, things, and animals, activating apparatus to introduce counteractive material into the area for neutralizing the nullifying material for adversely affecting the detector of first material;

removing the nullifying material from the area;

activating apparatus to lock down the area and impede entry to and exit from the area; and providing signals indicating the nullifying material is being introduced into the area, the nullifying material is being dispersed in the area, and an identity of the nullifying material.

2. The method of claim 1 wherein the nullifying material is olfactory-nullifying material.

3. The method of claim 1 wherein the detector of first material is an animal and the nullifying material is olfactory-nullifying material for inhibiting the sense of smell of the animal.

4. The method of claim 1 further comprising evacuating the nullifying material from the area.

5. The method of claim 1 further comprising emitting the nullifying material from a carrier, allowing the carrier to proceed a distance from the detector of first material, and stopping the carrier a distance apart from the detector of first material.

6. The method of claim 5 further comprising rendering the carrier inoperative or destroying the carrier.

7. The method of claim 1 wherein the detector of first material is mounted on a carrier, the carrier being one of a drone, a plane, a helicopter, a glider, an automobile, a tank, a train, a personnel carrier, a transporter, a boat, a subway, a raft, a snowmobile, a tracked vehicle, a robot, a trailer, a wheeled transport, a hovercraft, or a truck, the method further comprising moving the detector on the carrier with respect to the area.

* * * * *